United States Patent
Takahashi et al.

(10) Patent No.: US 6,302,985 B1
(45) Date of Patent: Oct. 16, 2001

(54) METHOD OF ADHERING COVER GLASS AND COVER GLASS ADHERING DEVICE

(75) Inventors: Kenji Takahashi, Koushoku; Kazuhisa Takeuchi, Togura-machi, both of (JP)

(73) Assignees: Kabushiki Kaisha Tiyoda Seisakusho, Nagano; Sakura Finetechnical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/382,835

(22) Filed: Aug. 25, 1999

(51) Int. Cl.$^7$ .................................................. G01N 1/28
(52) U.S. Cl. ............................ 156/99; 156/104; 156/295
(58) Field of Search ............................... 156/99, 103, 104, 156/87, 295, 286

(56) References Cited

U.S. PATENT DOCUMENTS 5,989,386 * 11/1999 Elliot ........................................ 156/285

FOREIGN PATENT DOCUMENTS

| 3-403697 | 6/1991 | (JP) . |
| 9-325105 | 12/1997 | (JP) . |
| 09325105A | * 12/1997 | (JP) ............................... G01N/1/28 |
| 10-104137 | 4/1998 | (JP) . |
| 10-197424 | 7/1998 | (JP) . |

* cited by examiner

Primary Examiner—Michael W. Ball
Assistant Examiner—Todd J. Kilkenny
(74) Attorney, Agent, or Firm—Jordan and Hamburg LLP (57) ABSTRACT

The method of the present invention is capable of securely removing air from a space between a cover glass and a slide glass and securely locating a damaged part of a specimen outside of a visual field of a microscope. One end of the cover glass is held by a sucking pad, which is provided to an arm capable of rotating and vertically moving. The cover glass is obliquely held with respect to the slide glass. The one end of the cover glass is held higher than the other end of the cover glass. A position of a rotational axis of the arm is moved to a position under the slide glass. The arm is rotated to make the other end of the cover glass contact the slide glass and curve the cover glass. The one end of the cover glass is gradually moved toward the slide glass.

33 Claims, 5 Drawing Sheets

METHOD OF ADHERING COVER GLASS AND COVER GLASS ADHERING DEVICE

BACKGROUND OF THE INVENTION

The present invention relates to a method of adhering a cover glass and a cover glass adhering device, more precisely relates to a method of adhering a cover glass, by which a cover glass is adhered onto a microscope specimen with a mounting medium, which are mounted on a slide glass, and a cover glass adhering device for executing said method.

A microscope specimen, e.g., a tissue slice of an affected part of a patient, is made by the steps of: slicing a tissue of the affected part; mounting the tissue slice on to a slide glass; removing fat from the tissue slice; dyeing the tissue slice; and adhering a cover glass, which covers over the tissue slice, onto the slide glass with mounting medium.

When the cover glass is adhered onto the slide glass, it is important to perfectly remove air bubbles, which obstruct observation through a microscope, from a space between the cover glass and the slide glass. Further, it is important for the observation to prevent the tissue slice from being damaged.

Figure 6:
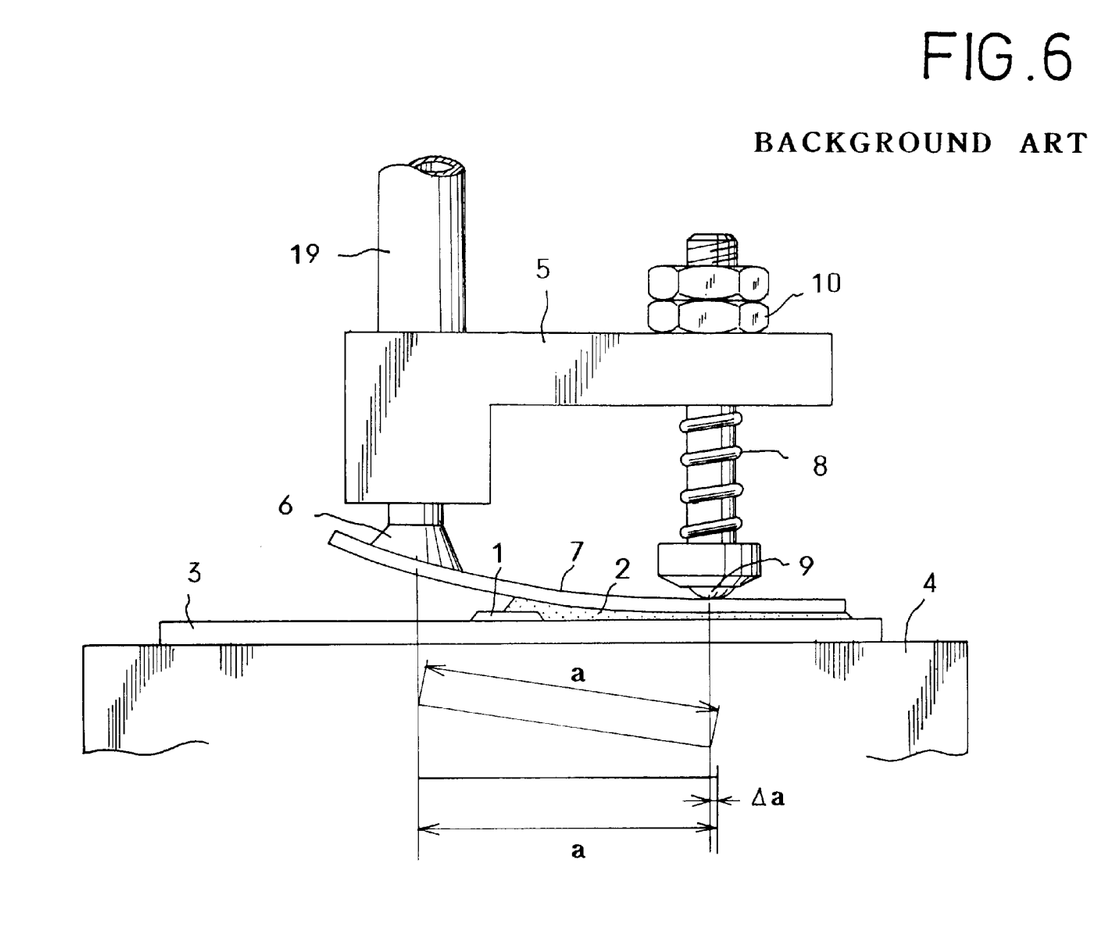
FIG. 6 is a front view of the conventional cover glass adhering device.

A conventional method of removing air bubbles is disclosed in Japanese Patent Publication Gazette No. 3-40367. FIG. 6 is a front view showing the method. A sliced specimen 1 in mounted on a slide glass 3. A mounting medium 2 is dropped onto the slide glass 3. The slide glass 3 is mounted on a table 4. A sucking pad 6 is provided to a holder 5, which can be moved in the vertical direction. The sucking pad 6 is moved downward, together with the holder 5, so as to hold a cover glass located at another place (not shown in FIG. 6). The sucking pad 6 holds one end of the cover glass 7 (a left end of the cover glass 7 shown in FIG. 6). The other end of the cover glass 7 (a right end of the cover glass 7 shown in FIG. 6) is downwardly biased by a pusher 9, which is downwardly biased by a spring 8, so as to obliquely hold the cover glass 7. The length of downward projection of the pusher 9 is adjusted by nuts 10, which are screwed with au upper part of the pusher 9 projected from an upper face of the holder 5.

Then the holder 5 is moved to a position above the slide glass 3, and the holder 5 is downwardly moved toward the slide glass 3. Firstly, the other end (the right end) of the cover glass 7 contacts an upper face of an end part of the slide glass 3, then an inner face of the cover glass 7 gradually contacts the slide glass 3 toward the one end (the left end). With this action, the mounting medium 2 is extended toward a left end of the slide glass 3 (see a state shown in FIG. 6).

After the cover glass 7, which is held by the sucking pad 6, is piled on and pushed onto the slide glass 3, the sucking pad 6 releases the cover glass 7 and the holder 5 is upwardly moved together with the sucking pad 6.

With this action, the slide glass 3, on which the microscope specimen 1 covered with the cover glass 7 is mounted, is left on the table 4.

Air existed in a space between the slide glass 3 and the cover glass 7 is pushed by the mounting medium 2 leftward when the cover glass 7 is gradually piled on and pushed onto the slide glass 3, so that the air is forced out from the space between the slide glass 3 and the cover glass 7 and no air bubbles are left therein.

When the cover glass 7 is piled on the slide glass 3, the left end of the cover glass 7, which is held by the sucking pad 6, is vertically moved downward. So, the right end of the cover glass 7, which has been obliquely held, is changed the posture horizontally. With this action, the right end of the cover glass 7 is slid a distance Δa (see FIG. 6). Namely, a part "a" (see FIG. 6) is moved from a oblique posture to a horizontal posture, so that the right end of the cover glass 7 is sidewardly slid against the pushing force of the pusher 9. An inner (lower) face of the right end of the cover glass 7 is slid on the upper face of the slide glass 3.

If the right end of the cover glass 7 is located on the specimen 1 when the right end of the cover glass 7 is slid on the slide glass 3, the specimen 1 will be damaged. If the damaged part of the specimen 1 is located under the cover glass 7, the damaged part obstructs the microscope observation.

To clearly observe the specimen 1 by the microscope, air must be perfectly removed from the space between the cover glass 7 and the slide glass 3. Further, the damaged part of the specimen 1, which has been damaged when the cover glass 7 is piled onto the slide glass 7, must not be located in a visual field of the microscope.

SUMMARY OF THE INVENTION

The present invention has been invented so as to solve an above described problem of the conventional method of adhering the cover glass.

An object of the present invention is to provide a method of adhering a cover glass, which is capable of perfectly removing air from a space between the cover glass and a slide glass and locating a damaged part of a specimen outside of a visual field of a microscope.

Another object of the present invention is to provide a cover glass adhering device which executes the method of the present invention.

The method of adhering a cover glass onto a specimen with a mounting medium, which are mounted on a slide glass, in a device including:

a horizontal shaft; an arm capable of rotating about the horizontal shaft and moving in the vertical direction; and a sucking pad being provided to the arm, the sucking pad being capable of sucking one end of the cover glass, which is located on the further side with respect to a rotational axis of the arm, comprises the steps of:

sucking the one end of the cover glass with the sucking pad;

obliquely holding the cover glass, above the slide glass, in a state in which the sucked one end of the cover glass is located on the upper side with respect to the other end thereof;

adjusting a position of the rotational axis of the arm so as to locate the same under the slide glass; and rotating the arm so as to make the other end of the cover glass contact the slide glass and curve the cover glass, and gradually moving the one end of the curved cover glass toward the slide glass, whereby air existed between the cover glass and the slide glass is forced out and the cover glass is adhered onto the slide glass.

In the method, an angle between a virtual line, which connects a center of the sucking pad and the rotational axis of the arm, and the cover glass may be an acute angle.

In the method, the one end of the curved cover glass may be gradually moved toward the slide glass with gradually reducing rotational speed of the arm. By gradually reducing the rotational speed of the arm, the mounting medium between the cover glass and the slide glass can be extended at fixed speed.

In the method, the rotational speed of the arm may be adjusted on the basis of properties of the mounting medium. By adjusting the rotational speed on the basis of the properties of the mounting medium, the air in the space between the cover glass and the slide glass can be perfectly removed.

The cover glass adhering device, comprises:

a table onto which a slide glass is mounted;

a supporting pillar being vertically provided to the table;

a supporting cylinder being provided to the supporting pillar, the supporting cylinder being capable of moving in the vertical direction, the supporting cylinder having a horizontal shaft;

means for moving the supporting cylinder in the vertical direction;

an arm being rotatably supported by the supporting cylinder, a base end of the arm being rotatably connected to the horizontal shaft of the supporting cylinder;

a sucking pad being provided to a front end of the arm;

means for rotating the arm; and means for controlling the moving means and the rotating means so as to suck one end of the cover glass, which is located on the further side with respect to a rotational axis of the arm, with the sucking pad; to obliquely hold the cover glass, above the slide glass, in a state in which the sucked one end of the cover glass is located on the upper side with respect to the other end thereof; to move the supporting cylinder downward until the horizontal axis reaches a position under the slide glass; and to rotate the arm to put the cover glass onto an upper face of the cover glass.

In the device, the controlling means may gradually reduce the rotational speed of the arm, and may further comprise means for gradually reducing the rotational speed of the arm when the one end of the cover glass is moved toward the slide glass.

In the present invention, the one end of the cover glass is sucked by the sucking pad; the cover glass is obliquely held above the slide glass and held in the state in which the sucked one end is located on the upper side with respect to the other end thereof; the cover glass is downwardly moved toward the slide glass in said state; and the arm is rotated to pile the cover glass onto the slide glass. With this action, the cover glass is curved and gradually piled onto the slide glass from the other end thereof. Thus, the air existed between the cover glass, and the air is forced out from the opened one end side. The air can be perfectly removed.

When the arm is rotated, the one end of the cover glass is sucked by the sucking pad and the position of the rotational axis of the arm is located under the slide glass, so that the damaged part of the specimen, which has been firstly made contact with the other end of the cover glass, is moved toward the one end of the cover glass. By moving the damaged part, the damaged part can be located near an edge of the cover glass, so that the damaged part can be removed from the visual field of the microscope.

Further, by adjusting the rotational speed of the arm on the basis of properties of the mounting medium so as to extend the mounting medium at fixed speed, forming air bubbles and overflowing the specimen from the cover glass can be securely prevented. Therefore, the microscope observation can be executed properly.

BRIEF DESCRIPTION OF THE DRAWINGS

Embodiments of the present invention will now be described by way of examples and with reference to the accompanying drawings, in which.

DETAILED DESCRIPTION OF THE PREFERRED EMBODIMENTS

Preferred embodiments of the present invention will now be described in detail with reference to the accompanying drawings.

Figure 1:
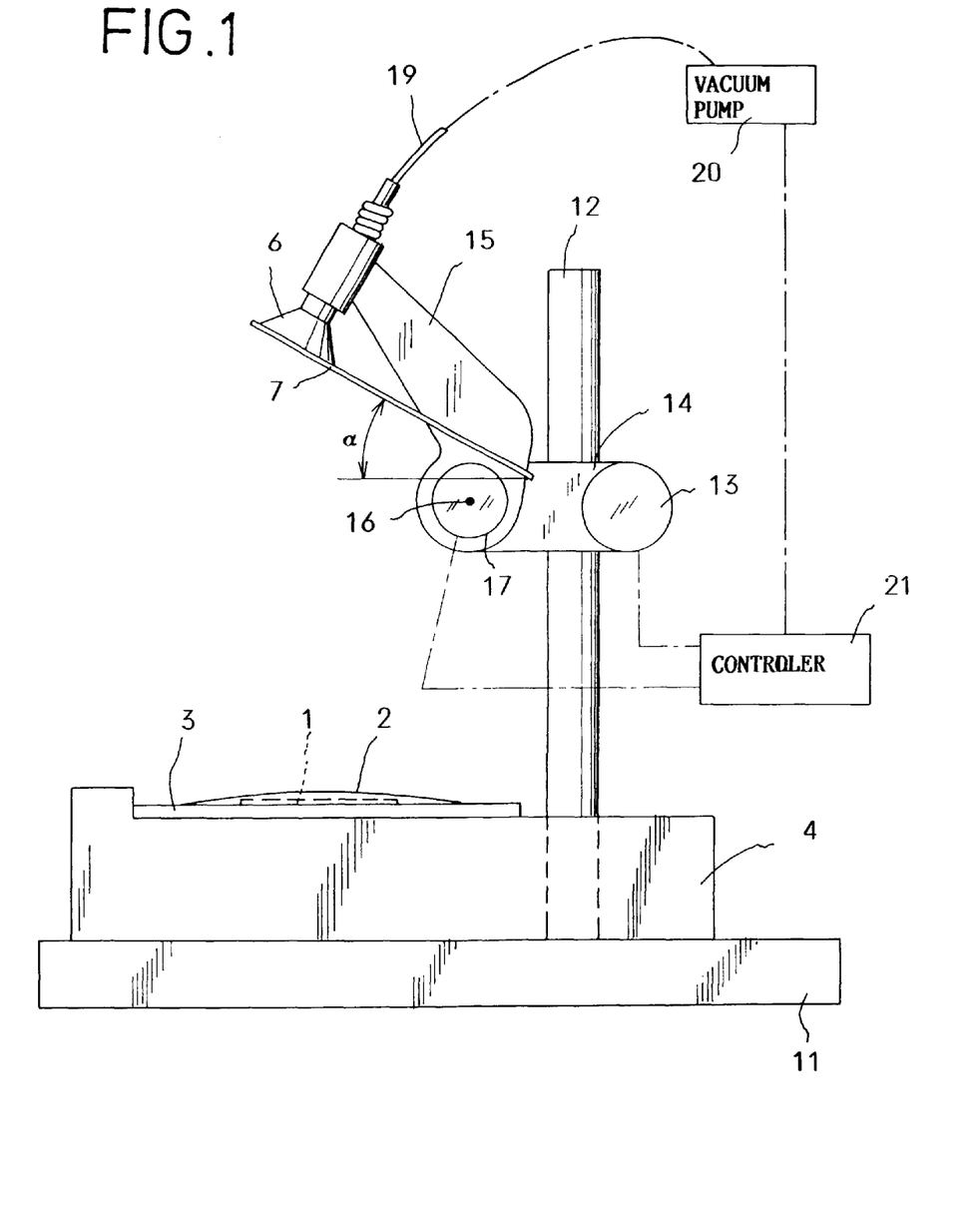
FIG. 1 is a front view of a cover glass adhering device of an embodiment of the present invention.
Figure 2:
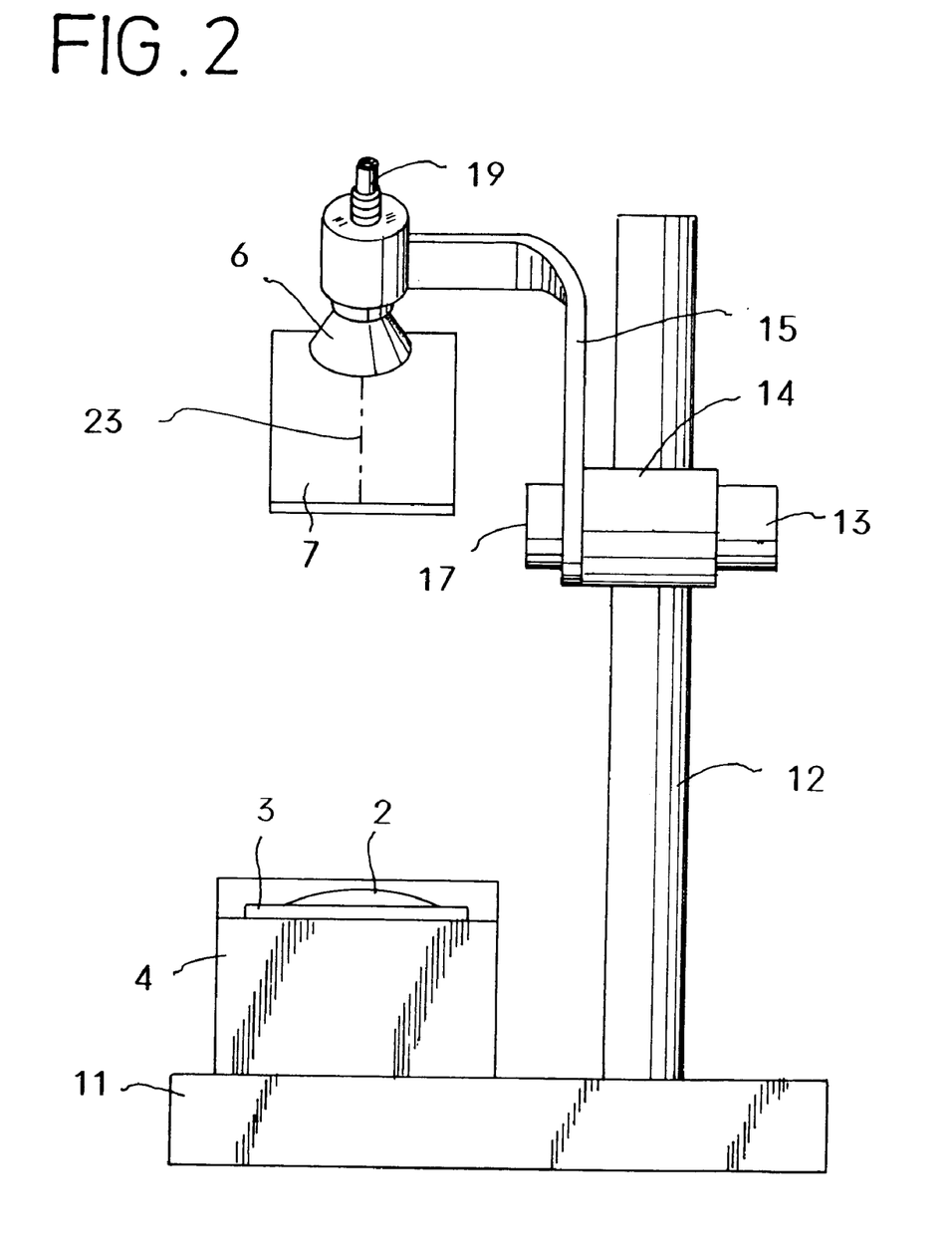
FIG. 2 is a side view of the cover glass adhering shown in FIG. 1.

A cover glass adhering device shown in FIGS. 1 and 2 includes: a table 4 being provided on a base 11; a supporting pillar 12 being provided to the table 4 and upwardly extended therefrom; a supporting cylinder 14 being provided to the supporting pillar 12 and capable of moving in the vertical direction; a motor 13, which is an example of the moving means, for moving the supporting cylinder 14 in the vertical direction; an arm 15 being rotatably supported by the supporting cylinder 14; a sucking pad 6 being provided to a front end of the arm 15 (an upper end of the arm 15 shown in FIGS. 1 and 2); a motor 17, which is an example of the rotating means, for rotating the arm 15; and a controller 21, which is an example of the controlling means. A specimen 1 included in a mounting medium 2 is mounted on a slide glass 3. The supporting cylinder 14 having the motor 13 covers the supporting pillar 12, which is vertically extended from a side part of the table 4. The supporting cylinder 14 is vertically moved, along the supporting pillar 12, by the motor 13.

The supporting cylinder 14 has a horizontal shaft 16. A base end of the arm 15 (a lower end of the arm 15 shown in FIGS. 1 and 2) is rotatably attached to the horizontal shaft 16. The arm 15 is rotated about the horizontal shaft 16 by the motor 17, which is provided to the base end of the arm 15.

The sucking pad 6, which is made of, e.g., rubber, vinyl is provided to the front end of the arm 15. An inner space of the sucking pad 6 is connected to a sucking port of a vacuum pump 20 by a flexible tube 19. A cover glass 7 is held by a lower sucking face of the sucking pad 6. Rotation of the both motors 13 and 17 and air-sucking action of the vacuum pump 20 are controlled by the controller 21.

Action of the cover glass adhering device, which adheres the cover glass 7 onto the slide glass 3, shown in FIGS. 1 and 2 will be explained.

Firstly, the one end of the cover glass 7 (the left end of the cover glass 7 shown in FIG. 1), which is located on the further side with respect to the horizontal shaft 16, which is a rotational axis of the arm 15, is sucked by the sucking pad 6, so that the cover glass 7 is held by the lower end face of the sucking pad 6. To hold the one end of the cover glass 7 by the sucking pad 6, the supporting cylinder 14 is upwardly moved by the motor 13 and the arm 15 is rotated, by the motor 17, until the lower end face of the sucking pad 6 reaches a horizontal position. Then, the cover glass 7, which has been located at another place (not shown), is moved close to the sucking pad 6 or the sucking pad 6 is moved, by rotating the supporting pillar 12, toward the cover glass 7, so that the cover glass 7 can be sucked and held by the sucking pad 6 as shown in FIGS. 1 and 2.

Next, the sucking pad 6 is moved upward by rotating the arm 15, in the clockwise direction, by the motor 17, so that the cover glass 7 is obliquely held, above the slide glass 3, in a state, in which the sucked one end of the cover glass 7 is located on the upper side with respect to the other end (the end close to the horizontal shaft 16). The inclination angle of the cover glass 7, with respect to the horizontal plane, is "α" (see FIG. 1).

Then, the supporting cylinder 14 is moved downward by the motor 13 so as to move the inclined cover glass 7 toward an upper face of the slide glass 3.

The supporting cylinder 14 is moved downward until the horizontal shaft 16, which is the rotational axis of the arm 15, reaches a position under the slide glass 3, which has been mounted on an upper face of the table 4. The arm 15 is rotated about the horizontal shaft 16 by the motor 17 so as to rotate the cover glass 7 in the counterclockwise direction. Note that, an angle "θ" between a virtual line 18, which connects a center of the sucking pad and the horizontal shaft 16, and the cover glass 7 is an acute angle.

Size of the cover glass 7 may be equal to or smaller than that of the slide glass 6. It may be optionally selected.

Figure 3:
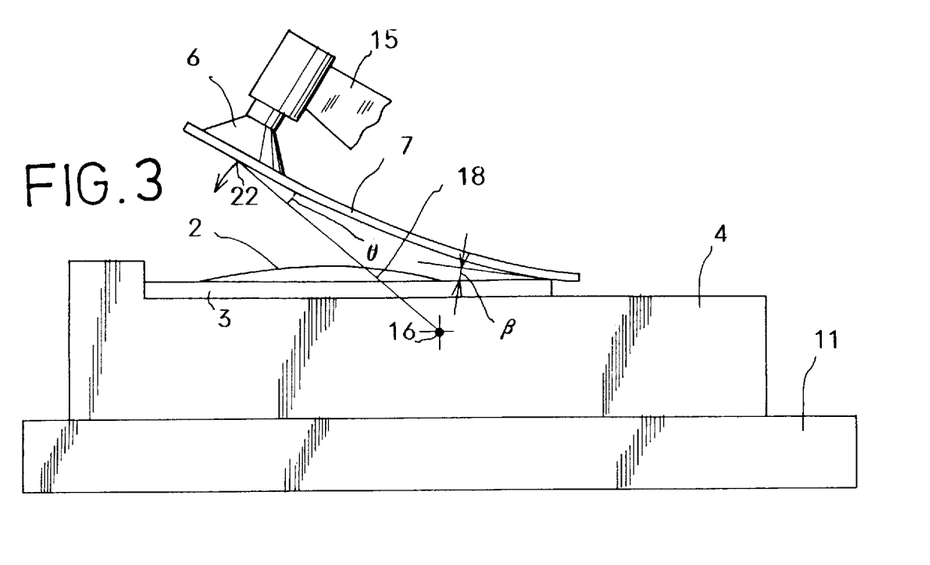
FIG. 3 is an explanation view of showing a state in which a cover glass, whose size is equal to that of a slide glass, is adhered onto the slide glass by the cover glass adhering device shown in FIGS. 1 and 2.

In FIG. 3, the size of the cover glass 7 is equal to that of the slide glass 3. The other end (the right end) of the cover glass 7 contacts an upper face of a right end part of the slide glass 3, and the cover glass 7 is curved.

Figure 4:
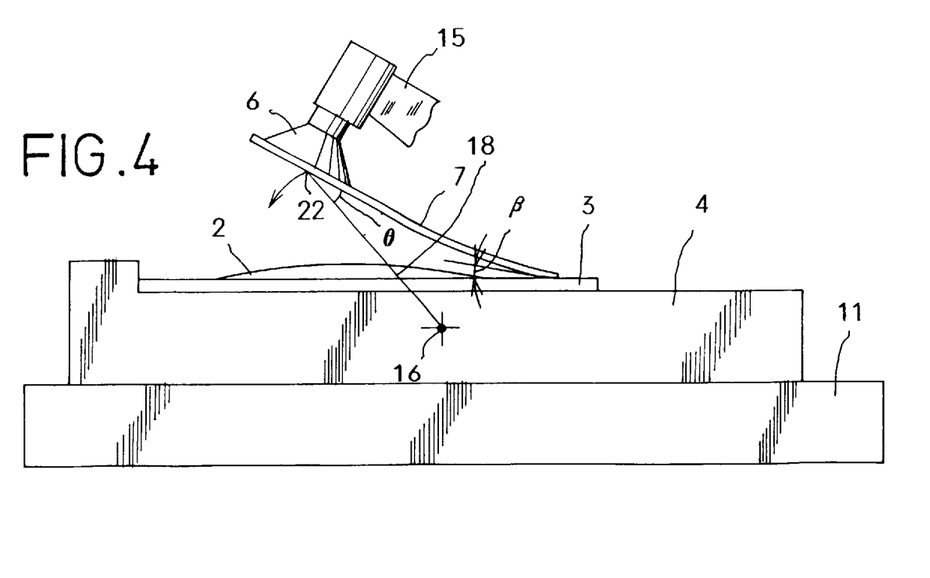
FIG. 4 is an explanation view of showing a state in which the cover glass, whose size is smaller than that of the slide glass, is adhered onto the slide glass by the cover glass adhering device shown in FIGS. 1 and 2.

On the other hand, in FIG. 4, the size of the cover glass 7 is smaller than that of the slide glass 3. The other end (the right end) of the cover glass 7 contacts an upper face of a right end part of the slide glass 3, and the cover glass 7 is curved as well.

The sucking pad 6 is gradually moved close to the slide glass 3 by rotating the arm 15; an angle "β" (see FIGS. 3 and 4) between the cover glass 7 and the slide glass 3 is gradually made narrower, and an lower face of the curved cover glass 7 gradually contacts the upper face of the slide glass 3 from the right end to the left end. When the cover glass 7 wholly contact the slide glass, the vacuum pump 20 releases the cover glass 7 from the sucking pad 6. When the cover glass 7 is released from the sucking pad 6, the sucking pad 6 is moved for the next operation.

Preferably, the vacuum pump 20 releases the cover glass 7 from the sucking pad 6 just before the cover glass 7 is wholly piled on the slide glass 3. The released cover glass 7 is piled and adhered on the slide glass 3 by its own weight and viscosity of the mounting medium 2. Therefore, the cover glass 7 is not excessively pressed onto the slide glass 3 by the arm 15, and the mounting medium 2 is not overflowed from the cover glass 7. No mounting medium is overflowed, so the cover glass 7 can be clear, the microscope observation is not obstructed, and the specimen can be easily treated. Since the angle "β" between the cover glass 7 and the slide glass 3 is gradually made narrower with moving the one end of the cover glass 7 toward the slide glass 3, the air existed in a space between the slide glass 3 and the cover glass 7 is forced out, from the opened one end of the cover glass 7, by the mounting medium 2 which extends toward the one end of the cover glass 7. Therefore, no air bubbles are formed in the space between the cover glass 7 and the slide glass 3.

Note that, above described action is automatically controlled by the controller 21, which controls the motors 13 and 17 and the vacuum pump 20.

Figure 5:
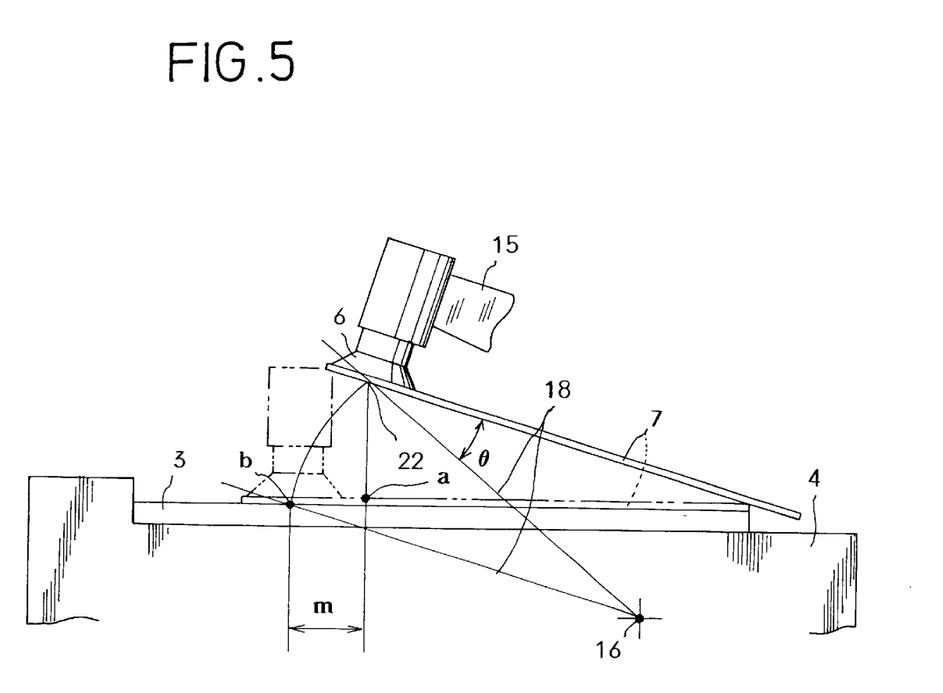
FIG. 5 is an explanation view showing a movement of the cover glass when the cover glass is adhered.

When the arm 15 is rotated in the counterclockwise direction, the horizontal shaft 16, which is the rotational axis of the arm 15, is located under the slide glass 3 as shown in FIG. 5. With this structure, by rotating the arm 15 so as to make the one end of the cover glass 7 contact the upper face of the slide glass 3, the center 22 of the sucking pad 6 is moved to a position "b" away from a position "a", which is immediately below the sucking pad 6 (see FIG. 5). Namely, the cover glass 7 is slid a length "m", which is equal to the distance between the positions "a" and "b", toward the position "b". By sliding the cover glass 7, the other end of the cover glass 7 is also moved toward the position "b". Therefore, contacting faces of the cover glass 7 and the slide glass 3 are moved leftward.

With this action, a part of the specimen 1, which is firstly made contact with the other end of the cover glass 7, is not located in the center part of the cover glass 7. Even if the part of the specimen 1 has been damaged by cover glass 7, the damaged part is not existed in the visual field of the microscope.

If the angle "θ" between the virtual line 18, which connects the center of the sucking pad and the horizontal shaft 16, and the cover glass 7 is at the right angle or an obtuse angle, the cover glass 7 cannot be gradually piled on to the slide glass 3 from the other end, so that the air can not be securely forced out from the space between the cover glass 7 and the slide glass 3.

In the case of the small cover glass 7 (see FIG. 4), a corner of the right end of the cover glass is slid on the upper face of the slide glass 3 leftward. Even if the right end of the cover glass 7 contacts a part of the specimen 1, the specimen 1 is not severely damaged, and the damaged part of the specimen 1 is not located in the visual field of the microscope.

On the other hand, in the case of executing the conventional method (see FIG. 6), the right end of the cover glass 7 is slid on the upper face of the slide glass 3 rightward. And, the cover glass 7 severely damages the specimen 1. Further, the severely damaged part of the specimen 1 is located in the visual field of the microscope, so that the microscope observation is obstructed.

In the present embodiment, if the inclination angle "α" of the cover glass 7, which has been sucked and held by the sucking pad 6, is 15°, the horizontal shaft 16, which is the rotational axis of the arm 15, is located 7.5 mm below the upper face of the slide glass 3 and the end of the cover glass 7 contacts a contact point, which is 5.5 mm from the right end of the slide glass 3, the cover glass 7 is moved about 2 mm toward the left end of the cover glass 7.

In the present embodiment, the cover glass 7 is gradually pressed onto the upper face of the slide glass 3 from the right end of the cover glass 7 to the left end thereof, so that the air existed in the space between the cover glass 7 and the slide glass 3 can be securely forced out form the opened left end of the cover glass 7. Therefore, no air bubbles are formed between the cover glass 7 and the slide glass 3.

If the rotational speed of the arm 15 to which the sucking pad 6 is attached is fixed, forming air bubbles cannot be securely prevented and the mounting medium 2 will be overflowed from the cover glass 7.

Dyeing agent for dyeing the specimen 1 is stuck on the upper face of the slide glass 3. To stably treat the specimen for a long time, a secular change of the dyeing agent must be prevented. To clearly observe the specimen 1, a refractive index of the mounting medium 2 should be adjusted. So, a clearing agent, e.g., xylem, has been previously coated on the upper face of the slide glass 3 so as to prevent the secular change of the dyeing agent and adjust the refractive index of the mounting medium 2.

However, it is difficult to uniformly coat the upper face of the slide glass 3 with the clearing agent, and the viscous mounting medium 2, which has an affinity for the clearing agent, will be ununiformly extended. Especially, if the rotational speed of the arm 15 having the sucking pad 6 is fixed, speed of extending the mounting medium 2 between the cover glass 7 and the slide glass 3 is accelerated with pressing the cover glass 7 onto the slide glass 3. By accelerating the extending speed of the mounting medium 2, the mounting medium 2 is ununiformly extended and air bubbles are apt to be formed between the cover glass 7 and the slide glass 3.

Further, by accelerating the extending speed of the mounting medium 2, the mounting medium 2 is apt to overflow from the cover glass 7. The overflowed mounting medium 2 obstructs the microscope observation, and treatment of the specimen becomes complicated.

To securely prevent forming air bubbles between the cover glass 7 and the slide glass 3 and overflowing the mounting medium 2 from the cover glass 7, the mounting medium 2 is extended at fixed speed when a distance between the lower face of the cover glass 7 and the upper face of the slide glass 3 is made shorter.

Note that, the extending speed, etc. of the mounting medium 2 are different according to properties thereof. Namely, degree of forming air bubbles in the mounting medium 2 and overflowing the mounting medium 2 are changed on the basis of amount, viscosity, density of the clearing agent, e.g., xylem, and the shape of the mounting medium 2 dispensed on the slide glass 3.

To stably adhere the cover glass 7 on the slide glass 3, securely prevent forming air bubbles between the cover glass 7 and the slide glass 3 and prevent overflowing the mounting medium 2 from the cover glass 7, rotational speed of the motor 17 (see FIGS. 1–5) is controlled.

In the case of employing the motor 17 whose rotational speed can be controlled, the rotational speed of the motor 17 is controlled by the controller 21. Namely, the rotational speed of the motor 17 is gradually reduced when the arm 15 is rotated about the horizontal shaft 16 to move the sucking pad 6 toward the slide glass 3.

Preferably, the controller 21 has a speed adjusting section, which is capable of adjusting the rotational speed of the motor 17. The speed adjusting section defines a rate of gradually reducing the rotational speed of the arm 15, on the basis of properties of the mounting medium 2, e.g., amount, viscosity, density of the clearing agent, the shape of the mounting medium 2 dispensed on the slide glass 3. The rotational speed of the arm 15 is gradually reduced when the one end of the cover glass 7 is moved toward the slide glass 3.

An inputted value of the speed adjusting section, which prevents forming air bubbles and overflowing the mounting medium 2, is previously defined on the basis of experiments.

By controlling the rate of gradually reducing the rotational speed of the arm 15 on the basis of the properties of the mounting medium 2 which is existed between the cover glass 7 and the slide glass 3, forming air bubbles and overflowing the mounting medium 2 from the cover glass 7 can be securely prevented, so that the microscope observation is not obstructed and treatment of the specimen becomes easy.

In the present example too, the vacuum pump 20 releases the cover glass 7 from the sucking pad 6 just before the cover glass 7 is wholly piled on the slide glass 3. Therefore, the cover glass 7 is not excessively pressed onto the slide glass 3, and the mounting medium 2 is not overflowed from the cover glass 7.

Note that, in the present example, the rate of reducing the rotational speed of the arm 15 is fixed so as to extend the mounting medium 2 between the cover glass 7 and the slide glass 3 at fixed speed. The extending speed of the mounting medium 2 may be gradually reduced with the rotation of the arm 15 so as to perfectly remove the air from the space between the cover glass 7 and the slide glass 3.

The cover glass is very thin, e.g., 0.06–0.25 mm, and must have excellent optical properties, so it is expensive.

Thus, the size of the cover glass is usually smaller than that of the slide glass. In the case of adhering the small cover glass by the conventional cover glass adhering device, the end of the cover glass is sometimes existed on the specimen and the damaged part of the specimen is left under the cover glass.

On the other hand, in the present invention, as described above, the air can be perfectly removed from the space between the cover glass and the slide glass and the damaged part of the specimen is not left under the cover glass, so that a clear visual field of the microscope can be gained.

Namely, the microscope observation is not obstructed by the damaged part.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of adhering a cover glass onto a specimen with a mounting medium, which are mounted on a slide glass, in a device including:
   a horizontal shaft;
   an arm capable of rotating about said horizontal shaft and moving in the vertical direction; and
   a sucking pad being provided to said arm, said sucking pad being capable of sucking one end of said cover glass, which is located on a further side of said cover glass with respect to a rotational axis of said arm;
   the method comprising the steps of:
   sucking the one end of said cover glass with said sucking pad;
   obliquely holding said cover glass, above said slide glass, in a state in which the sucked one end of said cover glass is located on an upper side of the cover glass with respect to the other end of the cover glass;
   adjusting a position of the rotational axis of said arm so as to locate the same under said slide glass; and
   rotating said arm so as to make the other end of said cover glass contact said slide glass and curve said cover glass, and moving the one end of said curved cover glass toward said slide glass while reducing rotational speed of said arm,
   whereby air existed between said cover glass and said slide glass is forced out and said cover glass is adhered onto said slide glass.

2. The method according to claim 1, wherein an angle between a virtual line, which connects a center of said sucking pad and the rotational axis of said arm, and said cover glass is an acute angle.

3. The method according to claim 1, wherein the rotational speed of said arm is adjusted on a basis of properties of the mounting medium so as to leave no air in the space between said cover glass and said slide glass when the one end of said cover glass is moved toward said slide glass with gradually reducing the rotational speed of said arm.

4. The method according to claim 1, wherein the arm is rotated to move the one end of the cover glass toward said slide glass such as to move a first contact portion of the cover glass, at which initial contact is made with the slide glass, toward a contact point at which the one end of the cover glass contacts the slide glass.

5. The method according to claim 4, wherein the arm is rotated to move the one end of the cover glass into contact with said slide glass.

6. The method according to claim 4, wherein the sucking of the one end is terminated prior to the one end of the cover glass contacting said slide glass.

7. The method according to claim 1, wherein the arm is rotated to move the one end of the cover glass into contact with said slide glass.

8. The method according to claim 1, wherein the sucking of the one end is terminated prior to the one end of the cover glass contacting said slide glass.

9. The method according to claim 1, wherein the rotation speed is reduced at a rate so as to extend the mounting medium at a fixed speed.

10. The method according to claim 1, wherein the rotation speed is reduced at a rate so as to extend the mounting medium at a decreasing speed.

11. A method of adhering a cover glass onto a specimen in a mounting medium on a slide glass, comprising the steps of:
holding one end of said cover glass, using a vacuum device applying suction, such that said cover glass is above said slide glass and oblique with respect to said slide glass, said one end of said cover glass being higher than another end of said cover glass opposite thereto;
moving said vacuum device along an arc of a circle having a circle center below said cover glass so as to initially dispose a contact area of said another end of said cover glass into contact with said slide glass;
further moving said vacuum device along said arc to move said one end toward said slide glass, after said contact area contacts said slide glass, while reducing a speed of movement of said vacuum device along said arc such that air between said cover glass and said slide glass is forced out; and
removing said suction to release said cover glass whereby said cover glass is adhered onto said slide glass.

12. The method according to claim 11, wherein a virtual line, connecting a center of said vacuum device and the circle center, and a plane of said cover glass define an acute angle maintained during said moving along said arc.

13. The method according to claim 12, wherein said step of further moving effects curving of said cover glass by contact with said slide glass.

14. The method according to claim 13, wherein the step of removing suction is effected prior to the one end of the cover glass contacting said slide glass.

15. The method according to claim 11, wherein said step of further moving effects curving of said cover glass by contact with said slide glass.

16. The method according to claim 15, wherein the step of removing suction is effected prior to the one end of the cover glass contacting said slide glass.

17. The method according to claim 11, wherein the step of further moving moves a first contact portion of the cover glass, at which initial contact is made with the slide glass, toward a contact point at which the one end of the cover glass contacts the slide glass.

18. The method according to claim 11, wherein the step of further moving moves the one end of the cover glass into contact with said slide glass.

19. The method according to claim 11, wherein the rotation speed is reduced at a rate so as to extend the mounting medium at a fixed speed.

20. The method according to claim 19, wherein a virtual line, connecting a center of said vacuum device and the circle center, and a plane of said cover glass define an acute angle maintained during said moving along said arc.

21. The method according to claim 20, wherein said step of further moving effects curving of said cover glass by contact with said slide glass.

22. The method according to claim 21, wherein the step of removing suction is effected prior to the one end of the cover glass contacting said slide glass.

23. The method according to claim 11, wherein the rotation speed is reduced at a rate so as to extend the mounting medium at a decreasing speed.

24. The method according to claim 23, wherein a virtual line, connecting a center of said vacuum device and the circle center, and a plane of said cover glass define an acute angle maintained during said moving along said arc.

25. The method according to claim 24, wherein said step of further moving effects curving of said cover glass by contact with said slide glass.

26. The method according to claim 25, wherein the step of removing suction is effected prior to the one end of the cover glass contacting said slide glass.

27. The method according to claim 11, wherein the speed of movement along the arc is adjusted on a basis of properties of the mounting medium so as to leave no air in the space between said cover glass and said slide glass when the one end of said cover glass is moved toward said slide glass while reducing the speed of movement.

28. A method of adhering a cover glass onto a specimen in a mounting medium on a slide glass, comprising the steps of:
holding one end of said cover glass, using a vacuum device applying suction, such that said cover glass is above said slide glass and oblique with respect to said slide glass, said one end of said cover glass being higher than another end of said cover glass opposite thereto;
moving said vacuum device so as to initially dispose a contact area of said another end of said cover glass into contact with said slide glass;
further moving said vacuum device along an arc of a circle having a circle center below said cover glass to move said one end toward said slide glass, after said contact area contacts said slide glass, while reducing a speed of movement of said vacuum device along said arc such that air between said cover glass and said slide glass is forced out; and
removing said suction to release said cover glass whereby said cover glass is adhered onto said slide glass.

29. The method according to claim 28, wherein a virtual line, connecting a center of said vacuum device and the circle center, and a plane of said cover glass define an acute angle maintained during said moving along said arc.

30. The method according to claim 28, wherein the step of further moving moves a first contact portion of the cover glass, at which initial contact is made with the slide glass, toward a contact point at which the one end of the cover glass contacts the slide glass.

31. The method according to claim 28, wherein the step of further moving moves the one end of the cover glass into contact with said slide glass.

32. The method according to claim 28, wherein the rotation speed is reduced at a rate so as to extend the mounting medium at a fixed speed.

33. The method according to claim 28, wherein the rotation speed is reduced at a rate so as to extend the mounting medium at a decreasing speed.

* * * * *